United States Patent [19]

Giannone

[11] 4,057,054
[45] Nov. 8, 1977

[54] EYE TREATMENT APPARATUS

[76] Inventor: Frank C. Giannone, 1416 N. Bridgeport Drive, Mount Prospect, Ill. 60056

[21] Appl. No.: 688,174

[22] Filed: May 20, 1976

[51] Int. Cl.² .............................................. A61H 5/00
[52] U.S. Cl. .................... 128/76.5; 33/200; 351/2; 351/158
[58] Field of Search .............. 128/76.5, 25 A; 33/200; 351/2, 3, 41, 158

[56] References Cited

U.S. PATENT DOCUMENTS

| 444,495 | 1/1891 | Johnston | 33/200 X |
|---|---|---|---|
| 742,081 | 10/1903 | Stierle | 128/76.5 |
| 3,603,305 | 9/1971 | Oppenheimer | 128/76.5 |

Primary Examiner—Robert W. Michell
Assistant Examiner—Michael H. Thaler
Attorney, Agent, or Firm—Leydig, Voit, Osann, Mayer & Holt, Ltd.

[57] ABSTRACT

This disclosure pertains to an eye treatment apparatus comprising a frame resembling a pair of eye glasses and including a lamp adjustably located within each of two eye piece areas. The lamps may each be adjusted in three directions and are powered by an intermittent source of electrical energy helpful in the treatment of strabismus, amblyopia, suppression and the restoration of normal binocular function.

5 Claims, 4 Drawing Figures

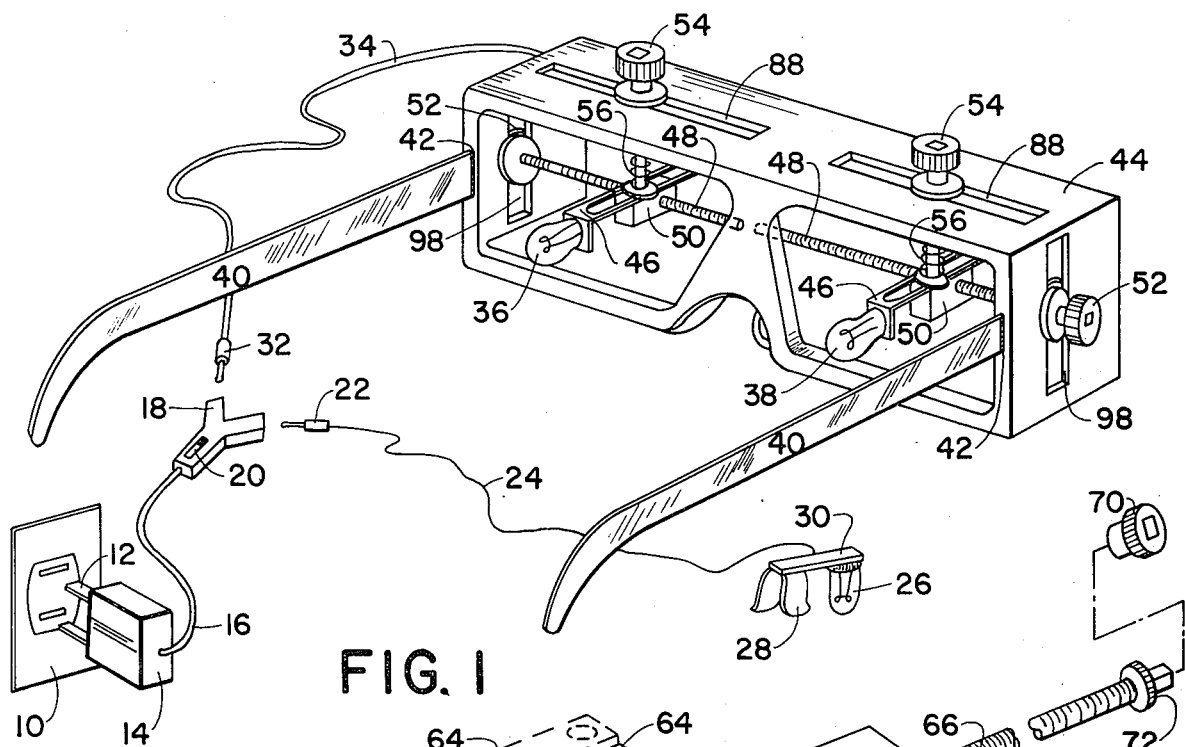
FIG. 1
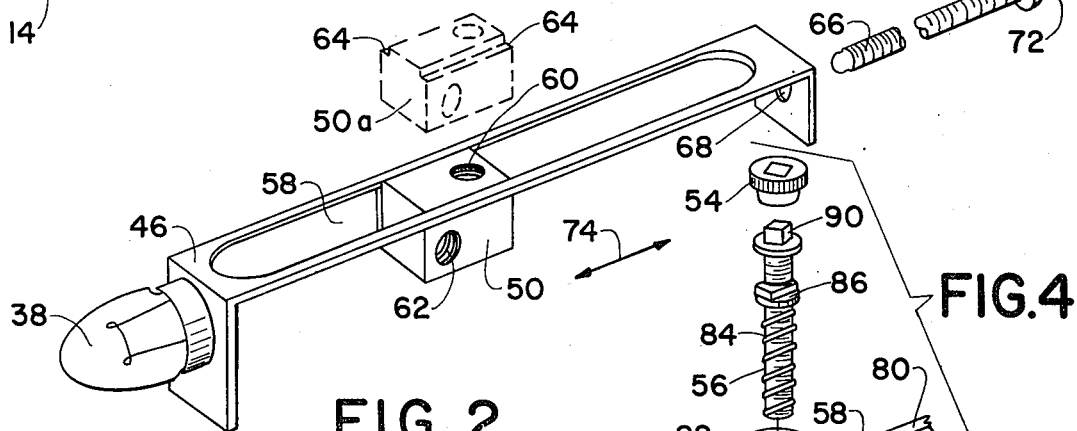
FIG. 2
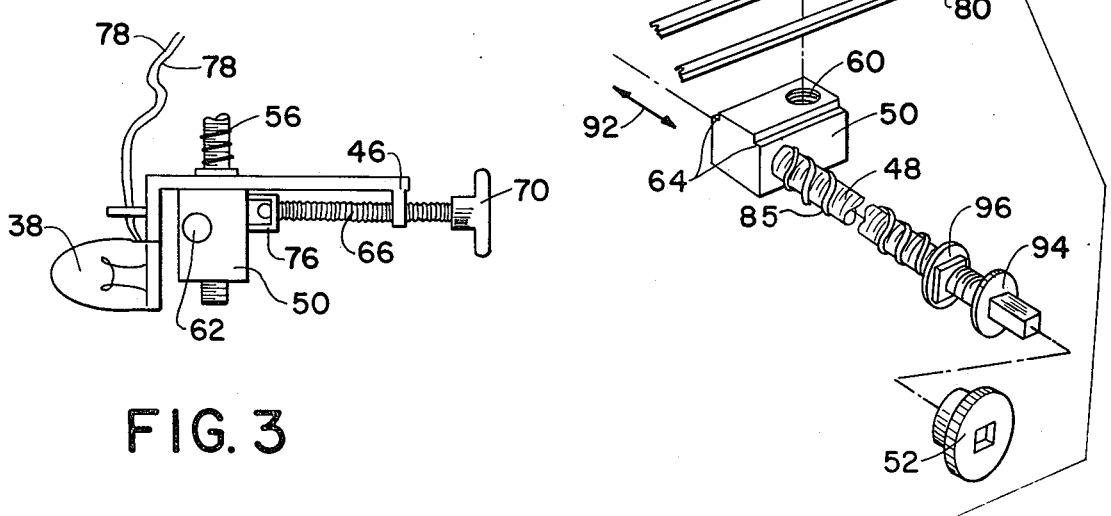
FIG. 3
FIG. 4

EYE TREATMENT APPARATUS

BACKGROUND OF THE INVENTION

1. The Field of the Invention

This invention relates to eye treating apparatus and more particularly to that class utilizing ear supported eye pieces containing flashing lamps.

2. Description of the Prior Art

The prior art includes a variety of devices for measuring and treating eyes employing illumination sources therefor. U.S. Pat. No. 3,547,528 issued on Dec. 15, 1970 to K. H. Weisfeld and U.S. Pat. No. 3,082,763 issued on Mar. 26, 1963 to S. C. McLaughlin Jr. both teach therapeutic or measuring devices employing flashing lights but are of such size and shape that they must be located in a stationary manner and are not suitably adjusted to accommodate to the physical characteristics of the patient, such as eye separation, intensity of illumination required to effectively treat the patient and to accommodate to the need of the patient to move about during the treatment process.

SUMMARY OF THE INVENTION

A primary object of the present invention is to provide a portable wearable dual lamp strabismus treating apparatus.

Another object of the present invention is to provide a pair of lamps each fully adjustable in horizontal and vertical directions as well as in depth of field before the user's eyes.

Still another object of the present invention is to provide a power pack operative from household utility voltage, which provides intermittent current sources to the lamps.

Yet another object of the present invention is to provide a flexible electrical cable providing operating current to a single lamp and clamp arrangement for fastening to the patients conventional eyeglasses powered by intermittent sources of electrical current.

Patients suffering from strabismus amblyopia suppression and abnormal binocular function have been treated successfully by routine therapeutic sessions utilizing intermittently flashing lamps to facilitate muscular training and to aid in the fixation process so that it may be voluntarily achieved and hopefully permanently maintained. Heretofore such therapeutic devices were stationary and cumbersome and lacked the ability to be accurately adjusted to the physical characteristics required by individual patients. The present invention provides an apparatus similar in appearance to a pair of eyeglasses except for the removal of the lens replaced by a pair of individual lamps, each functionally positioned to suit the needs of the individual patient and selectively intermittently illuminated. A common power supply supplies operating power optionally to the lamps or to a single lamp for selective mounting on the frame of the eyeglasses of the user. The adjustability and the lightweight construction of the present invention permits more efficacious treatment as well as increased comfort during use thereby minimizing patient resistance to periodic use.

These objects, as well as other objects of the present invention, will become more readily apparent after reading the following description of the accompanying drawings.

BRIEF DESCRIPTION OF THE DRAWINGS

FIG. 1 is a perspective view of the present invention.

FIG. 2 is a perspective view of the dual lamp mounting supports of the present invention.

FIG. 3 is a side elevational view of one of the dual lamp mounting supports of the present invention.

FIG. 4 is an exploded perspective view of the slide operating mechanism utilized in FIG. 1.

DESCRIPTION OF THE PREFERRED EMBODIMENT

The structure and method of fabrication of the present invention is applicable to a power supply comprising a household utility plug projecting from a housing containing a transformer and a flasher unit whose output circuit is connected to a dual receptacle device whose output terminals are controlled by an on-off selector switch.

One of the receptacles connects to a plug which is connected to a flexible cable supplying intermittent energizing power to an eyeglass frame fastening clip secured to an incandescent lamp.

Another plug, connects to another flexible cord which in turn provides energizing power, of the intermittent variety to a pair of lamps adjustably mounted to a frame whose appearance resembles that of a thick pair of conventional eyeglasses. Each lamp is mounted to slotted plates which can be adjusted to assume varying distances forward from the cornea as well as horizontally and vertically from the iris. Temples hingeably affixed to the housing serve in conventional fashion to position the housing supportably upon the ears as well as nose pieces, which provide an upward supporting force for the housing. Removable knobs permit the three dimensional adjustments for each lamp and prevent the unwanted adjustments of the positional locations of the lamps by the patient, thereby limiting the proper adjustment to the discretion of the treating physician.

Now referring to the figures and more particularly to the embodiment illustrated in FIG. 1 showing a household utility outlet 10 which may be utilized to provide electrical power to plug 12 affixed to housing 14. Housing 14 contains a miniature transformer, and if desired a rectifier circuit as well as a flasher unit. Wire 16 provides the output power from housing 14 to receptacle housing 18. On-off switch 20 controls the appearance of operating power at the output receptacles, not shown, and provides electrical energy through cable 24 to lamp 26. Clip 28, for fastening to the pair of eyeglasses of the user, is fixedly secured to bar 30 supporting lamp 26.

Plug 32 may also be connected to the output receptacles, not shown, and in turn provides operating current for flexible electrical cord 34 feeding lamps 36 and 38. Temples 40 are hingeably affixed at points 42 to housing 44. Slides 46 support lamps 36 and 38. Threaded members 48, fabricated from a helical spring wrapped around a resilient rod-like member engage blocks 50 and are used in conjunction with knobs 52 to enable blocks 50 to be moved along a line parallel to the forehead of the user. Knobs 54 similarly engage blocks 50 utilizing shafts 56 therefore. Knobs 52 and 54 have rectangular openings and may be removed from the shaft ends to which they are shown attached.

FIG. 2 illustrates lamp 38 fixedly secured to slide 46 and having elongated slot 58 therein. Block 50 engages the edges of slot 58 and is adapted with a pair of threaded holes 60 and 62. Block 50a, shown in dotted lines, is illustrated with shoulders 64 for engagement with the edges of slot 58. Threaded rod 66 engages the rear of block 50 rotatably whilst being threaded within hole 68. Knob 70 is removably engaged to rectangular shaped end 72 of shaft 66. When knob 70 is fitted to shaft end 72 and rotated in either direction, slide 46 may be urged in the direction of arrows 74 about supporting block 50.

FIG. 3 illustrates slide 46, threaded rod 66, and removable knob 70 fitted thereto. Clip 76 engages the free end of rod 66 by permitting the free rotation of rod 66 therewithin whilst preventing the axial displacement therefrom. Block 50 is shown supported below slide 46, having threaded rod 56 threadingly engage therethrough. Lamp 38 is electrically connected to wires 78 which are in turn electrically connected to cord 34, shown in FIG. 1.

FIG. 4 illustrates slot 58 formed partially between parallel guide members 80, a part of slide 46, shown in FIG. 2. Block 50 having shoulders 64 accept threaded rod 56 in hole 60 utilizing washer 82 and spring 84 to space block 50 a variable distance from shoulder 86, used to engage slots 88, shown in FIG. 1. Removable knob 54 is fitted to the free end 90 of shaft 56. Shaft 48 threadingly engages block 50 facilitating the position thereof along arrows 92 when knob 52 is fitted to end 94 of rod 48. Shoulder 96 engages slots 98, as shown in FIG. 1. A spring 85 spaces block 50 a variable distance from shoulder 96.

One of the advantages of the present invention is a portable wearable dual lamp strabismus treating apparatus.

Another advantage of the present invention is an eye treatment apparatus with a pair of lamps each fully adjustable in horizontal and vertical directions as well as in depth of field before the user's eyes.

Still another advantage of the present invention is an eye treatment apparatus with a power pack operative from household utility voltage, which provides intermittent current sources to the lamps.

Yet another advantage of the present invention is an eye treatment apparatus with a flexible electrical cable providing operating current to a single lamp and clamp arrangement for fastening to the patient's conventional eyeglasses powered by intermittent sources of electrical current.

Thus there is disclosed in the above description and in the drawings, an embodiment of the invention which fully and effectively accomplishes the objects thereof. However, it will become apparent to those skilled in the art, how to make variations and modifications to the instant invention. Therefore, this invention is to be limited not by the specific disclosure herein, but only by the appending claims.

The embodiment of the invention in which an exclusive privilege or property is claimed is defined as follows:

1. Eye treatment apparatus having, in combination, a hollow rectangular housing having at least a horizontal top wall, two vertical end walls and a front portion, two temple pieces connected to said housing and projecting outwardly from said front portion with one temple piece disposed adjacent each end of the housing whereby the housing may be supported on the head of a user with said front portion facing the user's eyes, said front portion having first and second openings, one on each side of the center of said front portion whereby each is generally alined with one of the user's eyes, first and second blocks disposed within said housing and generally alined with said first and second openings respectively, two lamps, means for supporting one of said lamps on said first block to shine through said first opening, means supporting the other of said lamps on said second block to shine through said second opening, means for connecting said lamps to an electrical power supply, said top wall having first and second longitudinal slots disposed respectively alongside said first and second openings, the end wall adjacent said first opening having a first vertical slot and the end wall adjacent said second opening having a second vertical slot, a first vertical threaded element projecting through said first longitudinal slot and threaded into said first block to adjust the vertical position of the first block, a first horizontal threaded member projecting through said first vertical slot and threaded into said first block to adjust the horizontal position of the first block, said two threaded elements constituting the sole means of support of said first block in said housing, a second vertical threaded element and a second horizontal threaded element similarly projecting respectively through said second horizontal and vertical slots and threaded into said second block thereby to constitute the sole support of the second block in said housing and to adjust the vertical and horizontal position of the block, and means operable to maintain the vertical and horizontal positions of said blocks.

2. Eye treatment apparatus as defined in claim 1 in which said means operable to maintain the positions of said blocks includes first parts fixed on each of said vertical elements and engaging the inside of said top wall, second parts fixed to said horizontal elements and engaging the insides of said end walls, first spring means acting between said blocks and said first parts to space said blocks from said first parts and second spring means acting between said blocks and said second parts to space said blocks from said second parts.

3. Eye treatment apparatus as defined in claim 2 in which said first spring means comprises two coiled springs, one encircling each of said vertical elements and each acting between the associated block and the associated first part and said second spring means comprises two coiled springs, one encircling each of said horizontal elements and each acting between the associated block and the associated second part.

4. Eye treatment apparatus as defined in claim 1 in which said means for supporting said lamps on said blocks includes two slides, one on each of said blocks and each carrying one of said lamps, each of said slides being mounted on the associated block to move horizontally toward and away from said front portion of said housing and two mechanisms, one for each of said slides and each including means operable to move one of said slides on its associated block to a preselected horizontal position and to hold said slide in said preselected position.

5. Eye treatment apparatus as defined in claim 4 in which each of said means of said mechanisms comprises a threaded element coacting between the associated slide and block to move the slide on the block when the threaded element is turned.

* * * * *